United States Patent [19]

Mukerji et al.

[11] Patent Number: 5,712,250
[45] Date of Patent: Jan. 27, 1998

[54] PRODUCT FOR INHIBITION OF HUMAN ROTAVIRUS INFECTION

[75] Inventors: Pradip Mukerji, Gahanna; Pedro Antonio Prieto, Columbus; Amanda Eun-Yeong Seo, Gahanna; Jeffrey Harris Baxter, Galena, all of Ohio; Richard Dale Cummings, Edmond, Okla.

[73] Assignees: Abbott Laboratories, Abbott Park, Ill.; University of Oklahoma, Oklahoma City, Okla.

[21] Appl. No.: 730,163

[22] Filed: Oct. 15, 1996

Related U.S. Application Data

[63] Continuation of Ser. No. 308,882, Sep. 16, 1994, abandoned.

[51] Int. Cl.[6] .......................... A61K 38/00; A61K 38/16; C12P 21/06; A23J 1/02
[52] U.S. Cl. ........................... 514/12; 514/2; 514/8; 514/21; 435/69.1; 426/657; 530/360
[58] Field of Search .................. 514/12, 2, 8, 21; 435/69.1; 530/360; 426/657

[56] References Cited

U.S. PATENT DOCUMENTS

| | | | |
|---|---|---|---|
| 5,147,853 | 9/1992 | Dosako et al. | 517/7 |
| 5,260,280 | 11/1993 | Isoda et al. | 514/25 |
| 5,505,955 | 4/1996 | Peterson et al. | 424/439 |
| 5,576,300 | 11/1996 | Mukerji et al. | 514/21 |

FOREIGN PATENT DOCUMENTS

| | | |
|---|---|---|
| 291265 | 5/1988 | European Pat. Off. |
| 488589 | 11/1991 | European Pat. Off. |
| WO93/15196 | 8/1993 | WIPO |
| WO94/09651 | 5/1994 | WIPO |
| WO94/15952 | 7/1994 | WIPO |

OTHER PUBLICATIONS

Brignon et al. (1985) Preparation and amino acid sequence of human kappa–casein, FEBS Letters 188 (1): 48–54, Aug. 1985.

Kitamoto et al., "Comparative Growth of Different Rotavirus Strains in Differentiated Cells (MA 104, HepG2, and CaCo-2)", Virology, 184:729–737 (1991).

Yolken et al., "Human Milk Mucin Inhibits Rotavirus Replication and Prevents Experimental Gastroenteritis", Journal of Clinical Investigation, 90:1984–1991 (1992).

Salf et al., "Cell culture propagation or a rotavirus," J. of Tissue Culture Methods: 149–156, 1988.

Terrett et al., "Physiochemical characterization of porcine pararotavirus & detection of virus & viral antibodies using cell culture immunofluorescence," J. of Clinical Microbiology 25:268–272, 1987.

*Primary Examiner*—Robert A. Wax
*Assistant Examiner*—Einar Stole
*Attorney, Agent, or Firm*—Donald O. Nickey; Thomas D. Brainard

[57] ABSTRACT

An enteral nutritional product containing either bovine κ-casein or human κ-casein at a concentration greater than that found in human or bovine milk and sufficient to inhibit infection of mammalian cells by human rotavirus.

3 Claims, 7 Drawing Sheets

MEDIUM CONTAINING $^{125}$I AND CELL LYSATES FROM HUMAN ROTAVIRUS INFECTED MA-104 CELLS ARE COLLECTED AFTER 1 OR 2 DAYS INFECTION

↓

EXTRACTION WITH TRICHLOROTRIFLUROETHANE

↓

CENTRIFUGATION AT 7000g FOR 30 MINUTES

↓

ULTRACENTRIFUGATION ON 20% SUCROSE CUSHION AT 90,000g FOR 3 HOURS

↓

ULTRACENTRIFUGATION ON 20% TO 60% SUCROSE GRADIENT AT 100,000g FOR 2.5 HOURS

↓

FRACTIONS ARE COLLECTED AND VIRUS CONTAINING FRACTIONS ARE IDENTIFIED BY COMPARING TO RADIOLABELED VIRUS STANDARD OR DETERMINED BY ELISA

FIG. 1

BSM: BOVINE SUBMAXILLARY MUCIN

BSM: BOVINE SUBMAXILLARY MUCIN

PRODUCT FOR INHIBITION OF HUMAN ROTAVIRUS INFECTION

This is a continuation of application Ser. No. 08/308,882 filed Sep. 16, 1994, now abandoned.

BACKGROUND OF THE INVENTION

1. Field of the Invention

This invention relates to a secretory protein, kappa-casein (κ-casein, which inhibits the attachment of human rotavirus (HRV) to mammalian cells.

2. Description of the Prior Art

Rotaviruses are the most important viral agents causing gastroehteritis in children living in both developing and developed countries (Yolken et al, "Human Milk Mucin Inhibits Rotavirus Replication and Prevents Experimental Gastroenteritis", Journal of Clinical Investigation 90, 1984–1991, 1992). Rotaviruses also cause diarrhea in nursing homes and day care centers, among travelers, in adults who have contact with children, and in immunocompromised patients.

Breast feeding provides some protection against enteric infections by pathogens when breast-fed infants are compared with bottle-fed babies. Studies of children living in developing and developed countries have shown that breast-fed infants have fewer episodes of gastroenteritis than bottle-fed infants. Breast feeding can also lessen the severity of diarrhea and vomiting associated with enteric diseases. However, breast-feeding does not provide total protection against infection and rotavirus infection has been observed in breast-fed infants.

No single factor has been found to be entirely responsible for the protective effect of breast feeding. It is believed that antibodies play a role, however, the level of anti-rotavirus antibody in human milk does not correlate with the degree of protection afforded by the milk. This suggests that non-immunoglobulin factors contribute to the protective effect of breast milk, and investigations have been undertaken to identify these factors.

Yolken et al. report a nonimmunoglobulin natural substance, milk mucin, that inhibits the replication of rotavirus. Mucin is a sialic acid-containing glycoprotein. In this report, Yolken et all demonstrate that mucin and mucinous components found in human milk show anti-rotaviral activity. Using purified milk mucin components in a solid-phase binding assay, Yolken et al. first showed mucin binding to African Green Monkey Kidney (MA-104) cells infected with human and simian strains of rotavirus. Using tissue culture techniques they next showed that a fraction of human milk, subsequently identified as human milk mucin complex, inhibited rotavirus replication. This was further demonstrated by showing that this fraction bound specifically to cells infected with rotavirus. When the active fraction was desialylated by chemical hydrolysis, there was a substantial decrease in binding to the rotavirus infected cells. This indicates that in the antiviral system reported here sialic acid is necessary for anti-rotaviral activity. Yolken et al. did not find evidence of rotavirus inhibitory activity in the lipid fractions of milk. Yolken et al. also demonstrated the efficacy of mucin-containing milk components in preventing experimental rotavirus gastroenteritis in suckling mice.

WO 94/09651 (Newburg et al., "Anti-Diarrheic Product and Method of Treating Rotavirus-Associated Infection") discloses a product containing an anti-diahrreal agent, such as the milk mucin complex and its components, which can bind rotavirus, and a method of inhibiting rotavirus infection in mammalian cells by exposing them to these agents.

U.S. Pat. No. 5,147,853 (Dosako et al., "Infection Protectant") discloses a method for preventing adhesion of E. coli to human epithelial cells by treating them with κ-casein, a sialic acid-conjugated protein derived from cow's milk.

The prevalence of rotavirus infection in the groups at risk, especially infants and children, and the seriousness of its effects attests to the need for an effective treatment. It is of particular importance to develop methods for prevention and treatment of rotavirus infection that have no adverse side effects.

BRIEF DESCRIPTION OF THE INVENTION

In the present invention it is disclosed that a secretory protein, κ-casein, which can be purified from human or bovine milk, or manufactured in recombinant form using cDNA, inhibits the attachment of human rotavirus to mammalian cells. In an assay, 60–70% inhibition of human rotavirus binding was obtained when the cells were treated with either human or bovine κ-casein. κ-casein, which is a mammary product believed to be without adverse side effects, can be used for the prevention and treatment of rotavirus infection.

BRIEF DESCRIPTION OF THE DRAWINGS

FIG. 1 shows the method of preparation of radioactive iodine labeled human rotavirus.

DETAILED DESCRIPTION OF THE INVENTION

Figure 2:
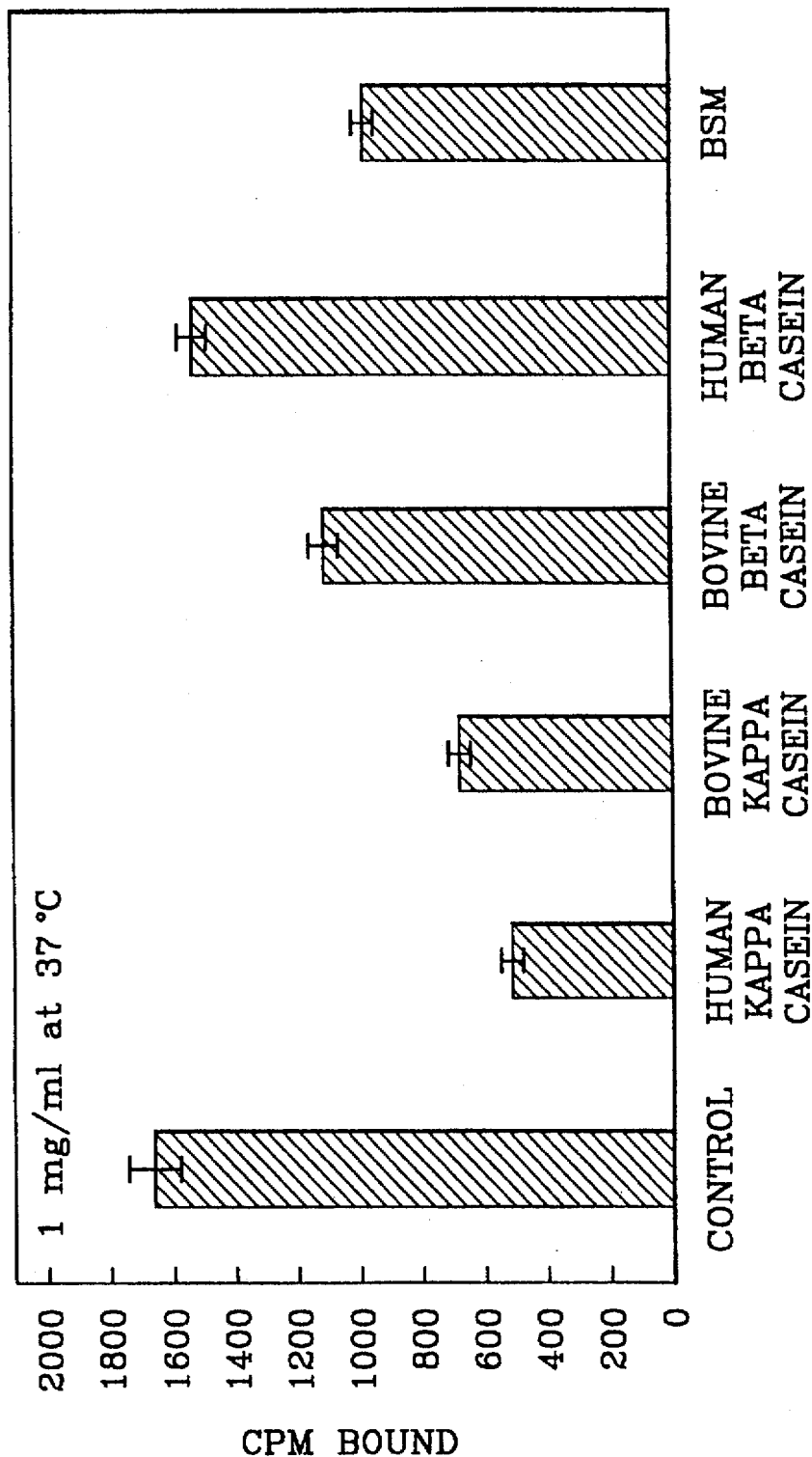
FIG. 2 is a graph showing the extent of inhibition of binding by human rotavirus to MA-104 cells by human and bovine κ-caseins.

This invention results from a research effort directed toward improving methods for preventing and treating enteric infections caused by rotavirus in mammals, especially in humans. The invention demonstrates the effectiveness of κ-casein in inhibiting the attachment of human rotavirus (HRV) to simian cells, and thereby preventing the virus from entering the cells and causing infection. The agent of this invention, κ-casein, is particularly useful in the treatment of infants and children as it is a normal constituent of human milk and is present in the human diet in bovine milk. It is, thus, unlikely to cause toxic or allergic reactions in treated subjects.

Bovine κ-casein is present in bovine milk at a concentration of about 3.3 grams/liter. It can be added to food preparations and made available to both adults and children at risk for rotavirus infection with little, if any, risk of immunological reaction.

What is disclosed in this application is an enteral nutritional product comprising an anti-rotaviral infection effective amount of an agent selected from the group consisting of native or recombinant unhydrolyzed human kappa-casein and native or recombinant unhydrolyzed bovine kappa-casein at a concentration exceeding that found in human or bovine milk; and a pharmaceutical composition comprising a therapeutically effective amount of the same agent.

Specific examples will now be provided to describe the methods of preparation of κ-casein and the two assays employed to measure inhibition of HRV-binding ability by human and bovine κ-casein. The examples are provided for purposes of illustration only and are not intended to be limiting.

EXAMPLE 1

Preparation of Human Milk Kappa-casein

Approximately 0.5 l of frozen human milk was thawed, centrifuged at 15,000×g for 1 hour at 4° C. and the fat pad, which is the top layer, was removed. The supernatant and pellet were homogenized and the pH of the resulting material was adjusted to 4.3 by the addition of hydrochloric acid. Calcium chloride was added to a final concentration of 60 mM. The mixture was stirred at room temperature for 1 hour and the precipitated caseins were then recovered by centrifugation at 18,000×g for 90 minutes at 4° C. Casein pellets were then dissolved in approximately 90 ml of 6M urea and 20 mM ethanolamine at a pH of 9.5 and extracted three times with 4 volumes of hexane to reduce the fat content further. The aqueous phase was dialyzed three times against 4 l of water using a 12,000 molecular weight cut-off membrane and lyophilized. This crude casein (yield was approximately 2–3 g/l) was dissolved in 6M urea, 20 mM n-2-hydroxyethylpeperazine-n'-2-ethane sulfonic acid (HEPES) (Sigma Chemical Co., St. Louis, Mo.) with 0.5% (V/V) 2-mercaptoethanol (2-ME) at Ph 7.5 and stirred at 4° C. for 1 hour. This solution was chromatographed in a 2.6×13 cm Macroprep-S® column (Bio-Rad, Hercules, Calif.) and equilibrated in the same buffer except that 0.1% (V/V) 2-ME was used. The washing buffer was 6M urea, 20 mM HEPES and 0.1% (V/V) 2-ME at pH 7.5. The eluant was monitored at a wavelength of 280 MM. Elution of the bound material was accomplished by application of a linear gradient from 0 to 0.3M sodium chloride in 100 minutes at a flow rate of 2 ml/minute. Fractions of 7 ml were collected and κ- casein was detected by comparison with human κ-casein obtained from SYMBICOM AB, Sweden used as a standard in sodium dodecyl sulfate-polyacrylamide gel electrophoresis (SDS-PAGE) or by immunoblot analysis. The fractions containing κ-casein were then pooled and dialyzed three times in 4 l of water as described above followed by lyophilization. This material was dissolved in 6M urea, 20 Mm HEPES and 0.5% (V/V) 2-ME at pH 7.0 at a concentration of approximately 10 mg/ml at 4° C. and loaded on the same column. The column was washed with 6M urea, 20 mM HEPES and 0.1% (V/V) 2-ME at pH 7.0 and then eluted with a linear gradient of 0 to 0.6M sodium chloride in 140 minutes at a flow rate of 2 ml/minute. The fractions containing the major peak at 280 MM were pooled, dialyzed as before and then lyophilized. The material was estimated to be of greater than 90% purity.

EXAMPLE 2

Source of bovine Kappa-casein

Bovine κ-casein was purchased from Sigma (catalog #C0406) and had a purity of greater than 80%.

EXAMPLE 3

Procedure for human rotavirus cell-binding inhibition assay

MA-104, African Green Monkey Kidney, cells (American Type Culture Collection, Md.) were grown on 24-well tissue culture plates to 100% confluency. The use of Ma-104 cells is described in Kitamoto et al., "Comparative Growth of Different Rotavirus Strains in Differentiated Cells", Virology 184:729–737 (1991). Experiments reported by Kitamoto et al. show that human rotaviruses, including the Wa strain, grow and produce antigen in MA-104 cells. The cells were washed twice with Hanks' medium (Sigma) and fixed with 1% paraformaldehyde in phosphate-buffered saline (PBS) at room temperature for 15 minutes. This was followed by three washes with tris-buffered saline (TBS). Solutions of potential inhibitors in TBS containing 5 mg/ml of bovine serum albumin (BSA) were added to the wells prior to the addition of $^{125}$I-labeled human rotavirus (HRV) suspensions. Radiolabeled virus was prepared as described in FIG. 1. The plates were incubated for 90 minutes at 37° C. and washed three times with TBS. The cells were then lysed by adding 0.2% sodium hydroxide and 2% SDS solution. Counts per minute (cpm) in the lysates were determined in a scintillation counter and used as indicators of cell-bound HRV.

EXAMPLE 4

Figure 3:
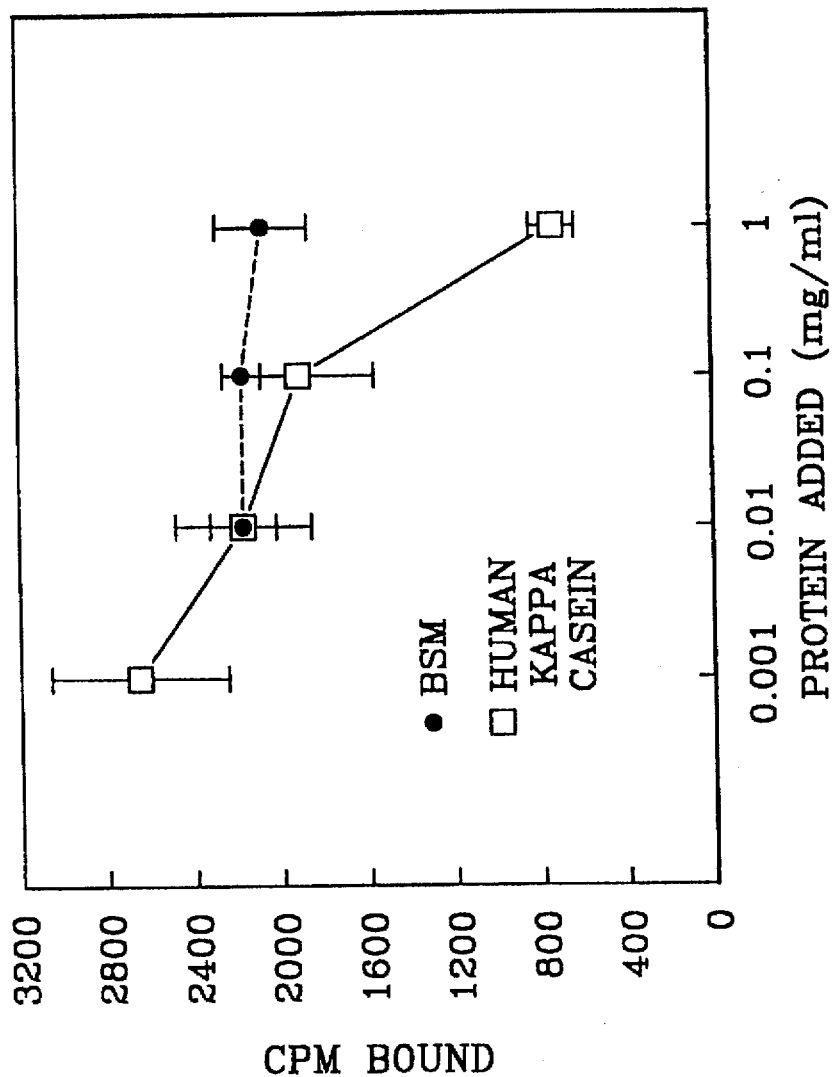
FIG. 3 shows the dose-dependent inhibition of human rotavirus to MA-104 cells by human κ-casein.

Determination of Inhibition of Binding of Human Rotavirus Strain Wa to MA-104 Cells by Human and Bovine Kappa-Caseins In an experiment shown in FIG. 2, five agents were tested for inhibitory potential at a concentration of 1 mg/ml. Human κ-casein inhibited binding by HRV strain Wa to MA-104 cells by more than 70% and bovine κ-casein (Sigma) inhibited binding by more than 60% when compared with control cells which did not receive any potential inhibitory agent after being exposed to HRV. Bovine beta-casein (Sigma) and human beta-casein (Symbicom AB, Sweden) exhibited much less ability to inhibit binding by HRV Wa. Bovine beta-casein showed 45% inhibition and human beta-casein showed 25% inhibition. Bovine submaxillary mucin (Sigma) was tested in the same experiment and showed 50% inhibition, however, further experimentation showed that this inhibition was not dose-dependent and, therefore, not specific. This is illustrated in FIG. 3. By contrast, human κ-casein was shown to be dose-dependent in the same experiment.

EXAMPLE 5

Figure 4:
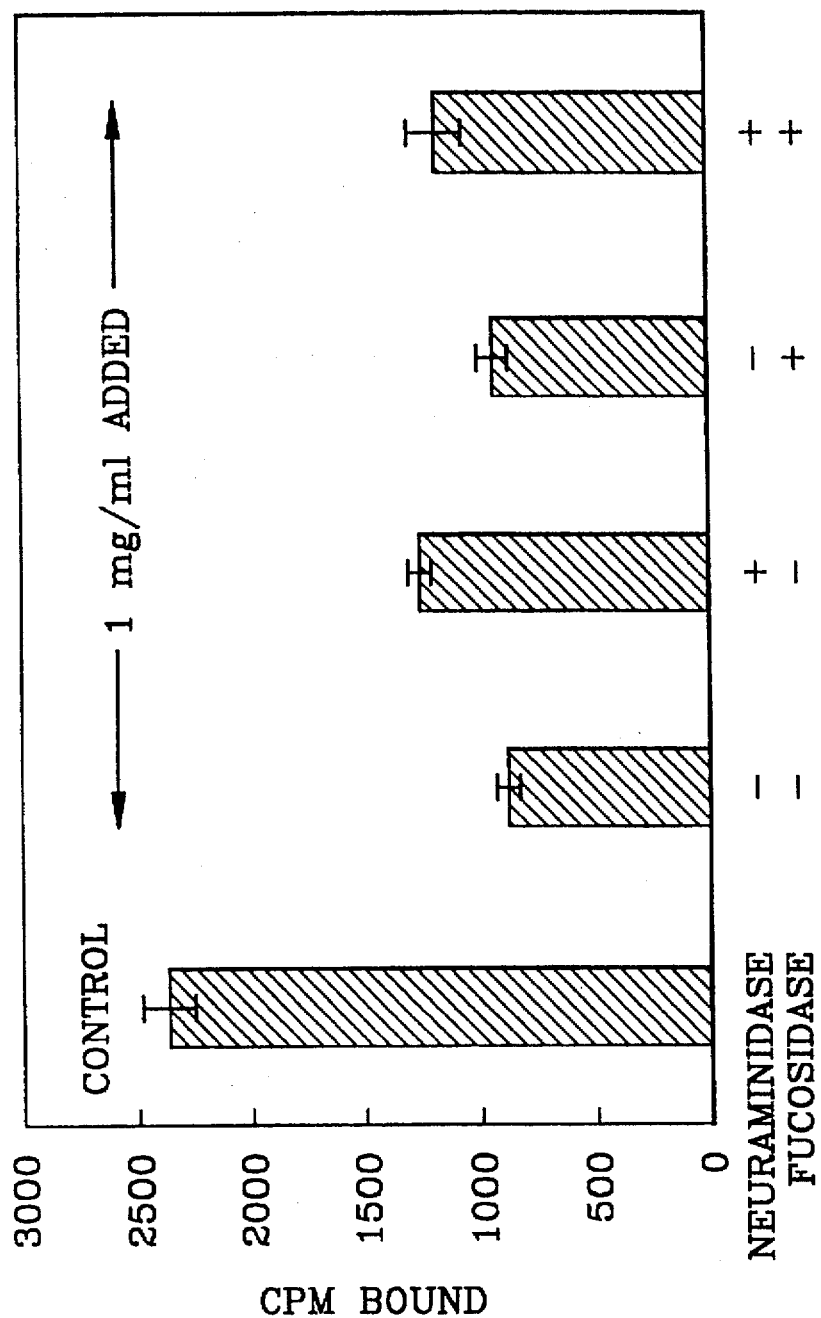
FIG. 4 shows that human κ-casein retained its ability to inhibit binding by human rotavirus to MA-104 cells after being treated with either neuraminidase, fucosidase or both.

Inhibition of Human Rotavirus Infection by Human or Bovine Kappa-Casein—Effect of Sialic Acid In another experiment using the procedure described in Example 3, human κ-casein was treated with neuraminidase to remove sialic acid from the glycan chains of the protein molecules. As illustrated in FIG. 4 the desialylated human κ-casein showed similar activity in the rotavirus inhibition assay to the intact human κ-casein. This indicates that in this experiment the sialic acid residues are not required for the inhibitory effect of human κ-casein. Intact and desialylated human κ-casein were then treated with fucosidase. Both treated agents retained their inhibitory activity, which is indicated in FIG. 4 This shows that under the conditions of this assay fucose residues on human κ-casein are not required for inhibitory activity against HRV.

Figure 5:
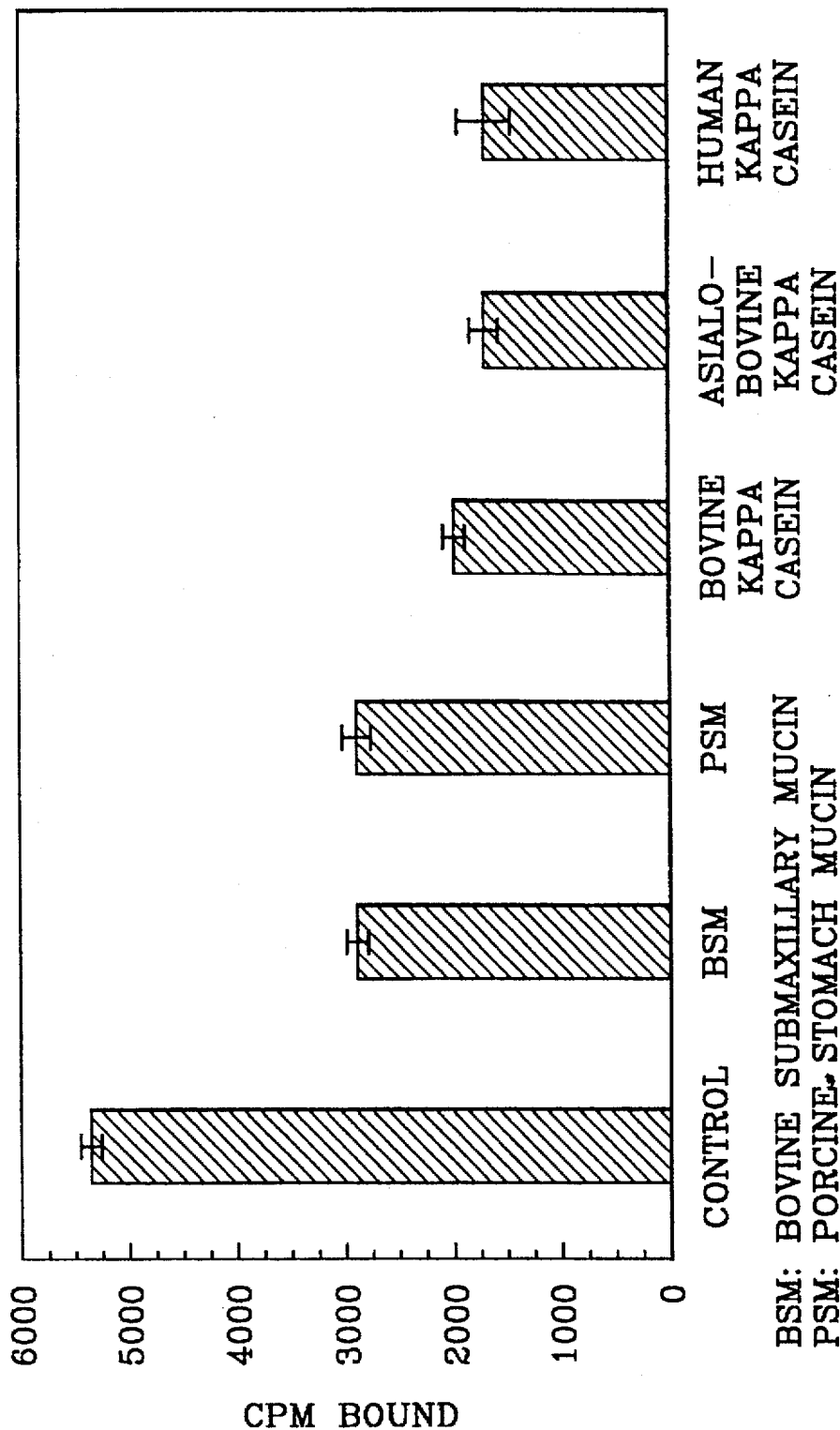
FIG. 5 shows that bovine κ-casein retained its ability to inhibit binding by human rotavirus to MA-104 cells after being treated with neuraminidase.

When bovine κ-casein was treated with neuraminidase to remove sialic acids, the resulting desialylated bovine κ-casein was highly active in this assay, as shown in FIG. 5. It is concluded that sialic acid residues on bovine κ-casein are also not required for activity against HRV.

EXAMPLE 6

Figure 6:
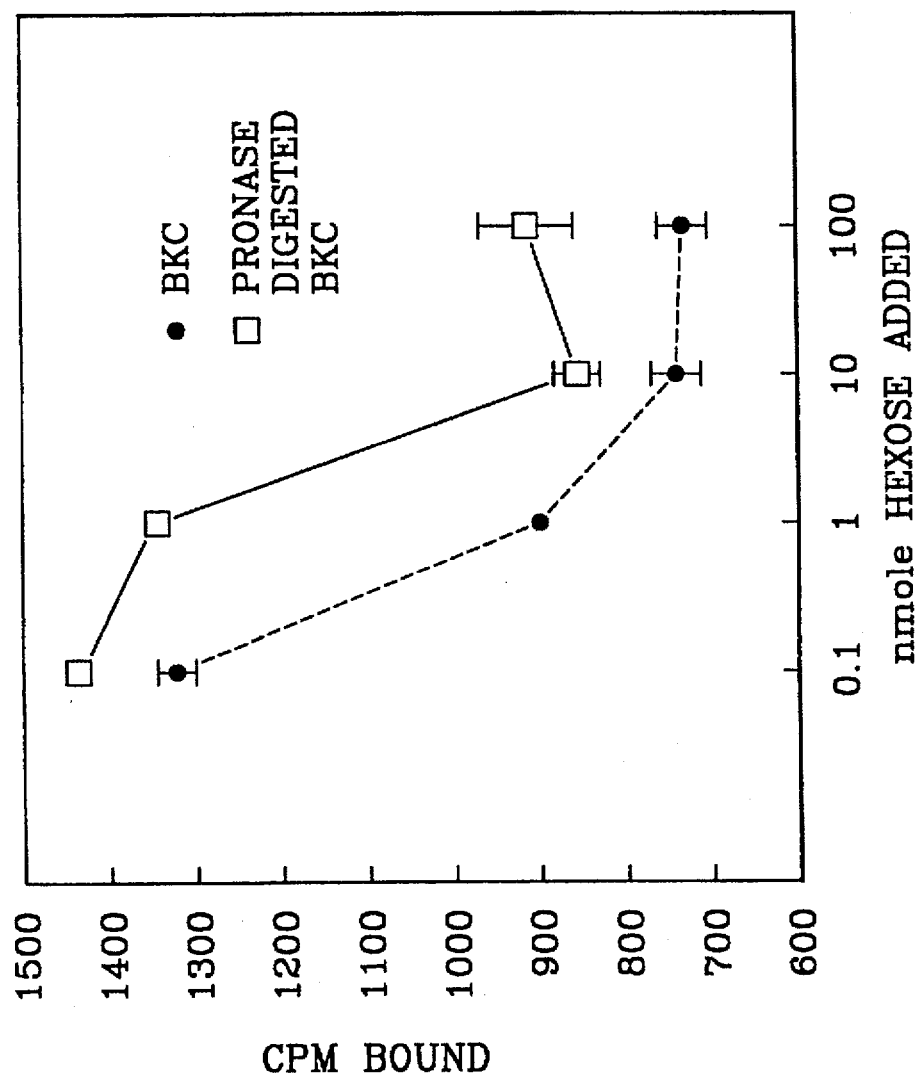
FIG. 6 shows the effect of digestion by Pronase® on the ability of bovine κ-casein to inhibit binding by human rotavirus to MA-104 cells.

Inhibition of Human Rotavirus Infection by Bovine Kappa-Casein—Effect of Hydrolysis Bovine κ-casein was digested in 100-fold excess with a protease, Pronase® (Calbiochem, La Jolla, Calif.), for 16 hours at 37° C. in 0.1M tris buffer at pH 8.0. FIG. 6 shows that the dose-dependent activity against HRV of the hydrolyzed protein was significant in this assay. The doses in this experiment were determined by the molar amounts of hexose present in the glycan chains of bovine κ-casein. Although 7-8 fold more of the hydrolyzed bovine κ-casein than native bovine κ-casein was required to achieve the same degree of inhibition, inhibitory activity against HRV was retained in the hydrolyzed protein under the conditions of this assay.

EXAMPLE 7

Inhibition of Human Rotavirus Infection—Second Assay Method—MA-104 Cells and Wa Strain of Human Rotavirus Another set of experiments was performed to measure the ability of bovine κ-casein to inhibit infection of cells by HRV. The assay procedure employed is as follows.

MA-104, African Green Monkey Kidney Cells whose use in rotavirus assays is described in Kitamoto et al, "Comparative Growth of Different Rotavirus Strains in Differentiated Cells", Virology 184:729–737 (1991), were obtained from BioWhittaker, Inc. (Walkersville, Md.). Experiments reported by Kitamoto et al. show that human rotaviruses, including the Wa strain, grow and produce antigen in MA-104 cells. The cells were cultured in Basal Medium Eagle (BME) (BioWhittaker) supplemented with 10% heat inactivated Fetal Bovine Serum (FBS) (Hyclone Laboratories, Logan, Utah) and 2 mM L-glutamine (BioWhittaker). Cells were routinely subcultured in 75 cm$^2$ flasks using trypsin-EDTA (0.25% trypsin, 1 Mm EDTA) (BioWhittaker) to detach cells.

Assay plates were treated with 1 µg/well of fibronectin (Sigma) to aid in the adhesion of cells to the culture substrate and to ensure their subsequent attachment during the wash steps of the virus neutralization assay. Fibronectin, solubilized in distilled water, was dispensed into each well and incubated for 1-3 hours at room temperature to allow binding to the plastic wells. Prior to dispensing the cells into the wells of the assay plate, the residual fibronectin was aspirated. Cells seeded into 96-well plates at a density of 10,000 cells per well with growth medium were maintained at 37° C. in a 5% $CO_2$ incubator for 3–4 days providing a confluent monolayer for virus neutralization studies.

Serotype 1 Wa strain of human rotavirus was obtained from Dr. Linda J. Saif (Ohio Agricultural Research and Development Center and was originally acquired from Dr. R. Wyatt (National Institutes of Allergy and Infectious Diseases). The virus stock used in these studies was a passage 5 viral harvest. Before use in these assays, HRV was activated with 10 IU/ml trypsin per 1 ml HRV and incubated for 30 minutes at 36° C. The virus was diluted with BME medium supplemented with 2 mM glutamine, 50 µg/ml gentamicin sulfate (BioWhittaker) and 1% penicillin-streptomycin solution (Sigma) to achieve a 1:250 dilution, which is twice the final desired virus concentration.

EXAMPLE 8

Inhibition of Human Rotavirus Infection—Second Assay Method—Virus Neutralization Equal volumes of test agent and trypsin-activated HRV were mixed and preincubated for 1 hour at room temperature to permit the test agent to bind to the virus. During the HRV+test agent preincubation period, plates containing MA-104 cells were washed 3 times with 15 µl diluent medium (150 µl/well/wash) after which another 50 µl of diluent medium was added to each well. MA-104 plates were then incubated at 37° C. in 5% $CO_2$ until the preincubation period for the HRV+test agent was completed. A control sample or 100 µl of the HRV+test agent sample was pipetted into appropriate wells and mixed with 50 µl of diluent medium. The plates were incubated for an additional 12–14 hours at 37° C. to allow the virus to propagate within the cells. Longer incubation time would result in infection of MA-104 cells by progeny virus, which is not desirable. Three types of control wells were included in each assay; (1) wells containing MA-104 cells, HRV, but no test agent, (2) wells containing MA-104 cells, HRV, and HRV antibodies, which are known HRV inhibitors and (3) wells containing MA-104 cells, but without virus. Each concentration of test agent or antibody was tested in triplicate.

After the incubation period, the assay plates were washed twice with Dulbecco's phosphate buffered saline (PBS) (BioWhittaker) 150 µl of cold 70% ethanol was added to each well and 95 µl was removed to prevent air from drying the cell monolayer. Cold absolute ethanol (190 µl ) was added to the 70% alcohol layer and the plates were rocked and refrigerated overnight. The alcohol was then removed and 150 µl of PBS containing 0.05% chick egg albumin (PBS-CEA) (Sigma) was added to each plate to block nonspecific binding sites.

To stain the plates, the PBS-CEA was removed and 200 µl of anti-rotavirus IgG was added to each well at a dilution of 1:2500. The plates were incubated for 30 minutes at room temperature. The plates were washed three times with PBS-CEA and 200 µl of peroxidase conjugated to anti-bovine IgG (Cappel Organon Teknika, Durham, N.C.) was added to each well at a dilution of 1:2000. The plates were covered and incubated for 30 minutes at room temperature. They were then washed three times with PBS-CEA and 100 µl of diaminobenzidine (Sigma) substrate was added to each well. The plates were incubated at room temperature for 20 minutes, washed twice with PBS-CEA and then washed with distilled water.

EXAMPLE 9

Figure 7:
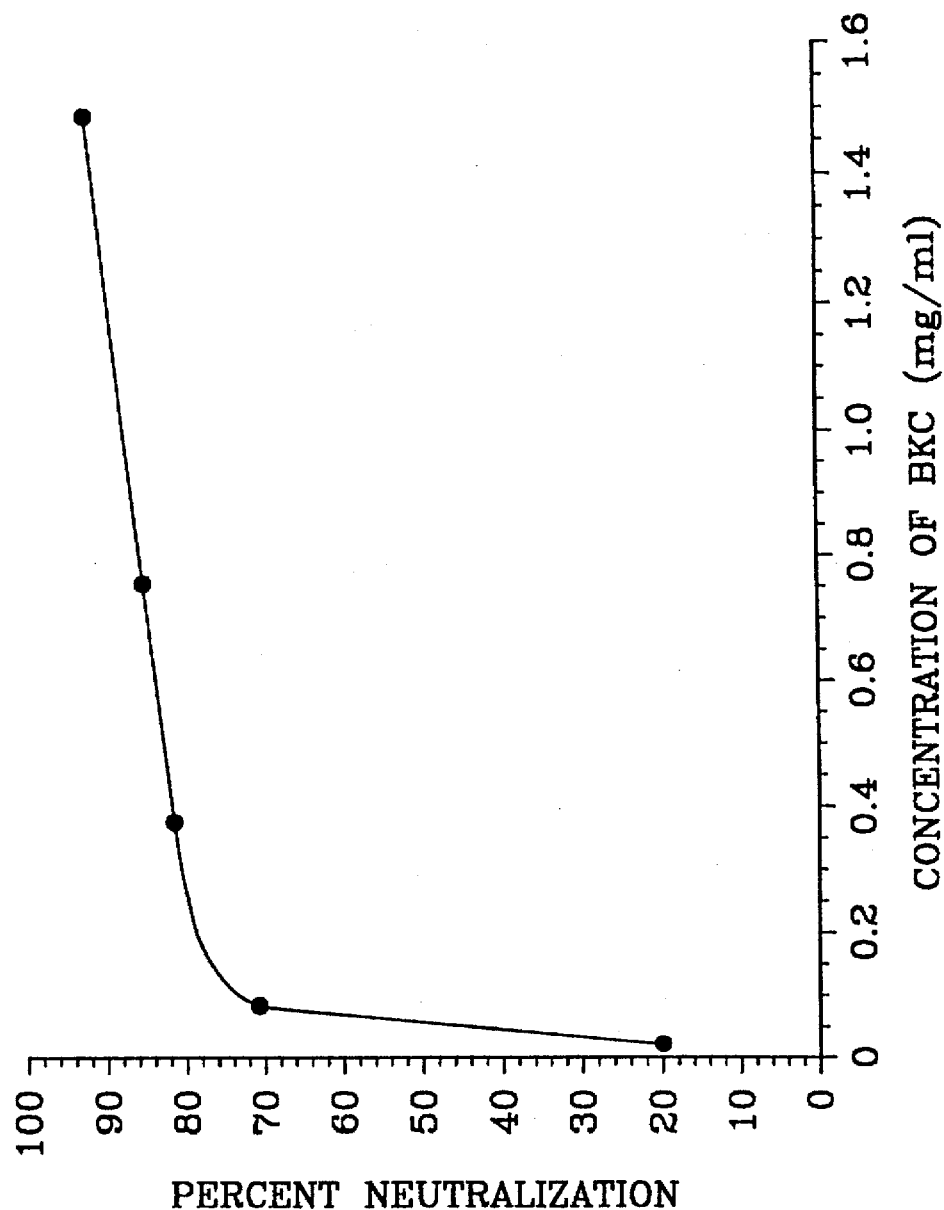
FIG. 7 shows the dose-dependent neutralization of human rotavirus as measured by the ability of bovine κ-casein to inhibit infection of MA-104 cells.

Inhibition of Human Rotavirus Infection by Bovine Kappa-Casein—Second Assay Method—Counting Infected Cells Plates which had been prepared according to the method of examples 7 and 8 were rehydrated by the addition of 150–200 µl of distilled water per well prior to microscopic examination. The plates were examined with a light microscope at 100% magnification. Cells which were darkly stained and contained characteristic brown and granular cytoplasmic regions were counted as virus-infected cells. A representative infected cell count was obtained for each well by counting all the stained cells within a uniform area which represented approximately 20% of the surface area of each well. Control wells, to which no virus had been added, were examined to ascertain that they were free of infected cells. Results were reported as percent inhibition obtained by comparing the average number of infected cells in the population which had been treated with test agent+HRV with the average number of infected cells in the population which had been exposed to virus alone. Results are shown in FIG. 7. Bovine κ-casein, the test agent, neutralized human rotavirus in a dose-dependant manner. Increased concentrations of bovine κ-casein resulted in correspondingly reduced levels of infection up to a concentration of 1.6 mg/ml where infection was inhibited by almost 90% and only 10% of cells were infected.

EXAMPLE 10

Inhibition of Human Rotavirus Infection by Bovine Kappa-Casein—Second Assay Method-Effect of Hydrolysis Bovine κ-casein was digested with Pronase® (Calbiochem), a protease, for either 4 hours or 20 hours and at the concentrations indicated in Tables 1 and 2, which show experiments run on different days. The plates were incubated at 37° C. according to the method of Example 8, and stained and counted according to the method of Example 9 to determine percent inhibition. The results of experiments performed on different days shown in Tables 1 and 2 indicate that hydrolysis of bovine κ-casein with the protease eliminated inhibition of infection of MA-104 cells by HRV. Undigested bovine κ-casein showed between 86% and 93% inhibition of viral attachment to Wa cells. Hydrolyzed bovine κ-casein showed either no inhibition or very slight inhibition in this assay. Pronase® alone, without the addition of bovine κ-casein to the plates, resulted in variable amounts of inhibition which were not dose-related.

In this assay, bovine κ-casein with Pronase® or Pronase® alone were boiled after the period of digestion to denature the protein and abolish its activity. Therefore, all inhibition of HRV which has been observed can be attributed to the action of the bovine κ-casein and not to the Pronase®. In the assay described in Example 6, Pronase® was not boiled sufficiently boiled after the initial digestion period. The results of that assay showed that hydrolysis did not abolish inhibition. It is likely that in that case the protease had not been completely inactivated and the inhibition observed may be attributed to residual Pronase® rather than to hydrolyzed bovine κ-casein.

TABLE 1

INHIBITION OF HUMAN ROTAVIRUS INFECTION BY BOVINE KAPPA-CASEIN: EFFECT OF HYDROLYSIS[1]

| TREATMENT | CONCENTRATION mg/ml | PERCENT INHIBITION |
| --- | --- | --- |
| BKC[2] 20 hrs/37° C. | 1.500 | 93 |
| BKC 20 hrs/37° C. | 0.750 | 97 |
| BKC 20 hrs/37° C. | 0.375 | 92 |
| BKC 4 hrs/37° C. | 1.500 | 86 |
| BKC 4 hrs/37° C. | 0.750 | 89 |
| BKC 4 hrs/37° C. | 0.375 | 87 |
| BKC+Pronase ™ 20 hrs/37° C. boiled | 1.500 | −19 |
| BKC+Pronase ™ 20 hrs/37° C. boiled | 0.750 | −6 |
| BKC+Pronase ™ 20 hrs/37° C. boiled | 0.375 | −7 |
| BKC+Pronase™ 4 hrs/37° C. boiled | 1.500 | −4 |
| BKC+Pronase ™ 4 hrs/37° C. boiled | 0.750 | −7 |
| BKC+Pronase ™ 4 hrs/37° C. boiled | 0.375 | −17 |
| Pronase ™ 20 hrs/37° C. boiled self-digested | 0.150 | −29 |
| Pronase ™ 20 hrs/37° C. boiled self-digested | 0.075 | −21 |
| Pronase ™ 20 hrs/37° C. boiled self-digested | 0.037 | −22 |
| Pronase ™ 4 hrs/37° C. boiled self-digested | 0.150 | −8 |
| Pronase ™ 4 hrs/37° C. boiled self-digested | 0.075 | −34 |
| Pronase ™ 4 hrs/37° C. boiled self-digested | 0.037 | −64 |

[1]Comparison of inhibition by bovine κ-casein, hydrolyzed κ-casein, and protease (Pronase ™) alone.
[2]Bovine kappa-casein

TABLE 2

INHIBITION OF HUMAN ROTAVIRUS INFECTION BY BOVINE KAPPA-CASEIN: EFFECT OF HYDROLYSIS[1]

| TREATMENT | CONCENTRATION mg/ml | PERCENT INHIBITION |
| --- | --- | --- |
| BKC+Pronase ™ 20 hrs/37° C. boiled | 1.5000 | 10 |
| BKC+Pronase ™ 20 hrs/37° C. boiled | 0.7500 | 6 |
| BKC+Pronase ™ 20 hrs/37° C. boiled | 0.3750 | −6 |
| Pronase ™ 20 hrs/37° C. boiled self-digested | 0.1500 | 54 |
| Pronase ™ 20 hrs/37° C. boiled self-digested | 0.0750 | 13 |
| Pronase ™ 20 hrs/37° C. boiled self-digested | 0.0375 | 8 |
| Pronase ™ 20 hrs/37° C. boiled self-digested | 0.0188 | 8 |
| Pronase ™ 20 hrs/37° C. boiled self-digested | 0.0094 | 15 |

[1]Comparison of hydrolyzed bovine κ-casein and protease (Pronase ™) alone.

EXAMPLE 11

Utility and Administration of Kappa-Casein

Human κ-casein can be extracted from human milk or can be obtained by recombinant DNA methods and cloning in prokaryotic or eukaryotic cells or from transgenic mammals using the DNA sequence and expression system of Hansson et al. Bovine κ-casein can be extracted from bovine milk where it is present at a concentration of approximately 3.3 grams/liter.

A DNA sequence encoding the human milk protein κ-casein is disclosed in PCT Publication No. WO 93/15196 (Hansson et al., "DNA Encoding Kappa-Casein, Process for Obtaining the Protein and Use Thereof"), which is being incorporated herein by reference for the purpose of teaching a method of constructing an expression system for a DNA sequence encoding a polypeptide with the biological activity of human κ-casein. The DNA sequence encoding human κ-casein is shown in SEQ ID NO: 1:, and the amino acid sequence of the polypeptide which it encodes is shown in SEQ ID NO: 2:. The encoded polypeptide was determined to have the antimicrobial activity or opioid activity of human κ-casein. The DNA sequence shown can be used in the production of recombinant human κ-casein using either a procaryotic or a eukaryotic system, or can be used to produce transgenic non-human mammals. Recombinant human κ-casein can be used as a constituent of infant formula to improve the nutritional and biological value of the formula or, as in the case of the present invention, to provide protection against enteric infection by human rotavirus.

The DNA sequence disclosed by Hansson et al. was determined from a cDNA clone isolated from a human mammary gland cDNA library. Construction of the expression system and its molecular biological characterization employed standard recombinant DNA methods. The procedure used was as follows: *E. coli* Y1090 bacteria were grown on LB (Luria-Bertoni) plates containing 50 µg/ml of carbenicillin. A single colony was isolated and grown overnight in a LB containing 0.2% maltose and 10 mM $MgSO_4$. 0.4 ml of the culture was then mixed with diluted library phages and adsorption was allowed for 15 minutes at 37° C. The infected culture was mixed with 7 ml soft agarose (0.75% agarose in LB and 10 mM $MgSO_4$). The soft agarose mixture was poured on 150 mm LB plates. The plates were incubated at 42° C. for about 3.5 hours until plaques were visible. Thereafter, each plate was overlaid with a membrane (DuPont NEN®, Colony Plaque Screen) previously saturated in 10 mM IPTG (Isopropyl-β-D-thiogalactoside), and incubated overnight at 37° C. The positions of the membranes were indicated before the membranes were removed. The membranes were washed in TTBS (tris buffered saline (TBS) containing 0.05% Tween 20), and incubated in TTBS containing 20% FCS and κ-casein antisera which had been raised in rabbits, purified, and diluted 1:25 for 2 hours at room temperature. The membranes were washed two times for 5 minutes in TTBS at room temperature. Biotinylated goat-antirabbit IgG in TBS (50mM Tris-HCl pH 7.9, 150 mM NaCl) was added and the membranes incubated for 1 hour at room temperature. The membranes were washed again with TTBS two times for 5 minutes at room temperature. The conjugate of streptavidin and biotinylated alkaline phosphatase in TTBS was added followed by an incubation for 1 hour at room temperature. The membranes were then washed four times in TTBS for 5 minutes and rinsed three times in a buffer containing 50 mM Tris-HCl pH 9.8, 3 mM $MgCl_2$, 50 µg/ml XP (5-bromo-4-chloro-3-indoylphosphate) and 100 µg/ml NBT (Nitroblue tetrasolium grade III). Approximately 100 positive plaques were identified.

The isolated plaques were purified by dilution and repeated screening. Phage DNA was prepared and the DNA preparations were digested with EcoRI. The digested DNA was separated by agarose electrophoresis and a number of EcoRI fragments were cloned into EcoRI digested and alkaline phosphatase treated pUC 18 plasmids and subsequently transformed into *E. coli* TG2. Transformants were selected on plates containing 50 µg/ml of carbenicillin, 40 µg/ml of X-gal (5-bromo-4-chloro-3-indoyl-β-D-galactoside) and 1 mM IPTC (Isopropyl-β-D-thiogalactoside). Plasmid DNA was analyzed from a number of transformants. A transformant harboring a plasmid containing the full-length cDNA fragment encoding human κ-casein was designated pS 270. Plasmid pS 70 DNA was subjected to restriction endonuclease analysis. The complete nucleotide sequence of both strands of the region encoding κ-casein was determined using a T7 sequencing kit (Pharmacia, Uppsala, Sweden) on double stranded templates as described by the vendor. Specific oligonucleotides complementary to pUC 18 or κ-casein sequences were used as primers for sequencing reactions.

The nucleotide sequence contained an open reading frame sufficient to encode the entire amino acid sequence of a κ-casein precursor protein consisting of 162 amino acids and a signal peptide of 20 amino acids.

Plasmid DNA, designated pS 270 was deposited in the collection of Deutsche Sammlung von Mikroorganismen und Zellkulturen GmbH, Mascheroder Weg 1 b, D.3300 Braunschweig, Germany and is identified by accession #DSM 6878.

Purified human or bovine κ-casein or their derivatives can be administered enterally in the form of an oral mucosal dosage unit or with a feeding tube, eg. nasojejunal or jejunal. In oral use, κ-casein should be between 2% and 50% by weight of the preparation. In pharmaceutical preparations, κ-casein should be mixed with a solid pulverulent carrier such as lactose, sorbitol, starch, or gelatin and pressed into tablet form. Multiple-unit dosages can also be prepared. Tablets and granules can be coated with substances such as polymers which change the dissolution rate in the gastrointestinal tract. Examples of coatings include anionic polymers having a pKa of above 5.5. Liquid preparations of human or bovine κ-casein can be prepared as 0.2% by weight of the active compound and glycerol. The daily dose of the active compound will vary with the administrative route.

The discovery disclosed herein of the antiviral activity of the secretory milk protein, κ-casein, makes feasible the use of the agent in infant formula, in pharmaceutical substances useful for the prevention and treatment of rotaviral infection in all groups at risk, as a nutritional supplement for patients undergoing antibiotic therapy, and as an ingredient in other bioactive enteral nutritional products. This list is meant to be suggestive and should not be interpreted as limiting the potential uses of κ-casein.

What is claimed is:

1. An enteral nutritional product comprising an antirotaviral agent selected from the group consisting of native unhydrolyzed human kappa-casein and recombinant unhydrolyzed human kappa-casein at a concentration exceeding that found in human milk.

2. The product of claim 1, wherein the enteral nutritional product is infant formula.

3. A pharmaceutical composition comprising a therapeutically effective amount of an agent selected from the group consisting of native unhydrolyzed human kappa-casein and recombinant unhydrolyzed human kappa-casein for the therapeutic or prophylactic treatment of infections of the gastrointestinal tract caused by human rotavirus.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH:857 base pairs
        ( B ) TYPE:Nucleic acid
        ( C ) STRANDEDNESS: Single
        ( D ) TOPOLOGY: Linear ( i i ) MOLECULE TYPE: cDNA
        ( A ) DESCRIPTION: Human milk kappa- casein ( i i i ) HYPOTHETICAL: No ( i v ) ANTI-SENSE:

( v ) FRAGMENT TYPE:

( v i ) ORIGINAL SOURCE: Human
        ( A ) ORGANISM: Homo sapiens
        ( B ) STRAIN:
        ( C ) INDIVIDUAL ISOLATE:
        ( D ) DEVELOPMENTAL STAGE: Adult
        ( E ) HAPLOTYPE:
        ( F ) TISSUE TYPE: Mammary gland
        ( G ) CELL TYPE:
        ( H ) CELL LINE:
        ( I ) ORGANELLE:

( v i i ) IMMEDIATE SOURCE: Human Mammary Gland
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: CDS
        ( B ) LOCATION: 45...593
        ( C ) IDENTIFICATION METHOD: DNA sequencing and restriction
            analysis
        ( D ) OTHER INFORMATION: The encoded product of nucleotide SEQ
            ID NO: 1: is the human milk protein, kappa-casein, having
            the amino acid sequence shown in SEQ ID NO: 2:.

( x ) PUBLICATION INFORMATION:
        ( A ) AUTHORS: L. Hansson et al
        ( B ) TITLE: DNA Encoding Kappa- Casein, Process for Obtaining
            the Protein and Use Thereof.
        ( C ) JOURNAL:
        ( D ) VOLUME:
        ( E ) ISSUE:
        ( F ) PAGES:
        ( G ) DATE:
        ( H ) DOCUMENT NUMBER: PCT/WO93/15196
        ( I ) FILING DATE:25-JAN-1993
        ( J ) PUBLICATION DATE:05-AUG- 1993
        ( K ) RELEVANT RESIDUES IN SEQ ID NO:

( x i ) SEQUENCE DESCRIPTION: SEQ ID NO: 1:

```
GAATTCGAG AGAAGACCTG ACTGGCACGA GGAAAGGTGC AATA ATG AAG AGT TTT           56
                                                Met Lys Ser Phe
                                                 1

CTT CTA GTT GTC AAT GCC CTG GCA TTA ACC CTG CCT TTT TTG GCT GTG          104
Leu Leu Val Val Asn Ala Leu Ala Leu Thr Leu Pro Phe Leu Ala Val
 5               10                  15                      20

GAG GTT CAA AAC CAG AAA CAA CCA GCA TGC CAT GAG AAT GAT GAA AGA          152
Glu Val Gln Asn Gln Lys Gln Pro Ala Cys His Glu Asn Asp Glu Arg
                 25                  30                      35

CCA TTC TAT CAG AAA ACA GCT CCA TAT GTC CCA ATG TAT TAT GTG CCA          200
Pro Phe Tyr Gln Lys Thr Ala Pro Tyr Val Pro Met Tyr Tyr Val Pro
             40                  45                  50

AAT AGC TAT CCT TAT TAT GGA ACC AAT TTG TAC CAA CGT AGA CCA GCT          248
Asn Ser Tyr Pro Tyr Tyr Gly Thr Asn Leu Tyr Gln Arg Arg Pro Ala
```

```
                    55                           60                           65
ATA  GCA  ATT  AAT  AAT  CCA  TAT  GTG  CCT  CGC  ACA  TAT  TAT  GCA  AAC  CCA        296
Ile  Ala  Ile  Asn  Asn  Pro  Tyr  Val  Pro  Arg  Thr  Tyr  Tyr  Ala  Asn  Pro
     70                       75                      80

GCT  GTA  GTT  AGG  CCA  CAT  GCC  CAA  ATT  CCT  CAG  CGG  CAA  TAC  CTG  CCA        344
Ala  Val  Val  Arg  Pro  His  Ala  Gln  Ile  Pro  Gln  Arg  Gln  Tyr  Leu  Pro
85                            90                      95                      100

AAT  AGC  CAC  CCA  CCC  ACT  GTG  GTA  CGT  CGC  CCA  AAC  CTG  CAT  CCA  TCA        392
Asn  Ser  His  Pro  Pro  Thr  Val  Val  Arg  Arg  Pro  Asn  Leu  His  Pro  Ser
               105                           110                          115

TTT  ATT  GCC  ATC  CCC  CCA  AAG  AAA  ATT  CAG  GAT  AAA  ATA  ATC  ATC  CCT        440
Phe  Ile  Ala  Ile  Pro  Pro  Lys  Lys  Ile  Gln  Asp  Lys  Ile  Ile  Ile  Pro
               120                           125                     130

ACC  ATC  AAT  ACC  ATT  GCT  ACT  GTT  GAA  CCT  ACA  CCA  GCT  CCT  GCC  ACT        488
Thr  Ile  Asn  Thr  Ile  Ala  Thr  Val  Glu  Pro  Thr  Pro  Ala  Pro  Ala  Thr
               135                      140                     145

GAA  CCA  ACG  GTG  GAC  AGT  GTA  GTC  ACT  CCA  GAA  GCT  TTT  TCA  GAG  TCC        536
Glu  Pro  Thr  Val  Asp  Ser  Val  Val  Thr  Pro  Glu  Ala  Phe  Ser  Glu  Ser
     150                      155                          160

ATC  ATC  ACG  AGC  ACC  CCT  GAG  ACA  ACC  ACA  GTT  GCA  GTT  ACT  CCA  CCT        584
Ile  Ile  Thr  Ser  Thr  Pro  Glu  Thr  Thr  Thr  Val  Ala  Val  Thr  Pro  Pro
165                      170                          175                     180

ACG  GCA  TAAAAACACC  AAGGAAATAT  CAAAGAACAC  AACGCAGGAC  TTGCTGAAAC                  640
Thr  Ala

CAAATTACTA  CTTCACACTC  TCCTTCAGCC  ATTTGTCTGC  CTTCAGTCAA  CAGAAAATGT                700

GATTTTCACA  GATTCAGCTC  TTCTCTCCTT  ACATTTACA   TTCATGCCAC  ATTCAATATT                760

TTGATTCTTG  CACAATAAAG  CCAACTGATT  GCAAAAAAAA  AAAAAAAAAA  AAAAAAAAA                 820

AAAAAAAAAA  AAAAAAAAAA  AAAAAAAAAA  CGAATTC                                          857
```

( 2 ) INFORMATION FOR SEQ ID NO: 2:

( i ) SEQUENCE CHARACTERISTICS:
        ( A ) LENGTH:182 amino acids
        ( B ) TYPE:Amino acid
        ( C ) STRANDEDNESS:
        ( D ) TOPOLOGY: Linear ( i i ) MOLECULE TYPE: Protein.
        ( A ) DESCRIPTION:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:

(A) NAME/KEY:
(B) LOCATION:
(C) IDENTIFICATION METHOD:
(D) OTHER INFORMATION:

(x) PUBLICATION INFORMATION:
(A) AUTHORS: L. Hansson et al
(B) TITLE: DNA Encoding Kappa- Casein, Process for Obtaining the Protein and Use Thereof.
(C) JOURNAL:
(D) VOLUME:
(E) ISSUE:
(F) PAGES:
(G) DATE:
(H) DOCUMENT NUMBER: PCT/WO93/15196
(I) FILING DATE: 25-JAN-1993
(J) PUBLICATION DATE: 05-AUG-1993
(K) RELEVANT RESIDUES IN SEQ ID NO:

(xi) SEQUENCE DESCRIPTION: SEQ ID NO: 2:

```
Met Lys Ser Phe Leu Leu Val Val Asn Ala Leu Ala Leu Thr Leu Pro
 1               5                  10                  15
Phe Leu Ala Val Glu Val Gln Asn Gln Lys Gln Pro Ala Cys His Glu
            20                  25                  30
Asn Asp Glu Arg Pro Phe Tyr Gln Lys Thr Ala Pro Tyr Val Pro Met
        35                  40                  45
Tyr Tyr Val Pro Asn Ser Tyr Pro Tyr Gly Thr Asn Leu Tyr Gln
    50                  55                  60
Arg Arg Pro Ala Ile Ala Ile Asn Asn Pro Tyr Val Pro Arg Thr Tyr
 65                  70                  75                  80
Tyr Ala Asn Pro Ala Val Val Arg Pro His Ala Gln Ile Pro Gln Arg
                85                  90                  95
Gln Tyr Leu Pro Asn Ser His Pro Pro Thr Val Val Arg Arg Pro Asn
            100                 105                 110
Leu His Pro Ser Phe Ile Ala Ile Pro Pro Lys Lys Ile Gln Asp Lys
        115                 120                 125
Ile Ile Ile Pro Thr Ile Asn Thr Ile Ala Thr Val Glu Pro Thr Pro
    130                 135                 140
Ala Pro Ala Thr Glu Pro Thr Val Asp Ser Val Val Thr Pro Glu Ala
145                 150                 155                 160
Phe Ser Glu Ser Ile Ile Thr Ser Thr Pro Glu Thr Thr Thr Val Ala
                165                 170                 175
Val Thr Pro Pro Thr Ala
                180
```